US012690847B2

(12) United States Patent
Sottile et al.

(10) Patent No.: US 12,690,847 B2
(45) Date of Patent: Jul. 28, 2026

(54) GENERATING ULTRASOUND PROTOCOLS

(71) Applicant: FUJIFILM SONOSITE, INC.,
Bothell, WA (US)

(72) Inventors: Anthony Sottile, Bothell, WA (US);
David Knapp, Bellevue, WA (US)

(73) Assignee: FUJIFILM SONOSITE, INC.,
Bothell, WA (US)

( * ) Notice: Subject to any disclaimer, the term of this
patent is extended or adjusted under 35
U.S.C. 154(b) by 0 days.

(21) Appl. No.: 18/400,777

(22) Filed: Dec. 29, 2023

(65) Prior Publication Data

US 2025/0213228 A1     Jul. 3, 2025

(51) Int. Cl.
A61B 8/00 (2006.01)
A61B 8/08 (2006.01)
A61B 90/00 (2016.01)

(52) U.S. Cl.
CPC .............. A61B 8/54 (2013.01); A61B 8/4444
(2013.01); A61B 8/463 (2013.01); A61B 8/468
(2013.01); A61B 8/5207 (2013.01); **A61B
8/565 (2013.01); A61B 90/06 (2016.02); A61B
2090/065 (2016.02); A61B 2562/0219**
(2013.01)

(58) Field of Classification Search
CPC ......... A61B 8/54; A61B 8/4444; A61B 8/463;
A61B 8/468; A61B 8/5207; A61B 8/565;
A61B 90/06; A61B 2090/065; A61B
2562/0219
See application file for complete search history.

(56) References Cited

U.S. PATENT DOCUMENTS

| | | | | |
|---|---|---|---|---|
| 9,354,709 | B1 * | 5/2016 | Heller ................... | G06F 1/1694 |
| 2003/0097054 | A1 * | 5/2003 | Sasaki ................... | A61B 8/565 |
| | | | | 600/407 |
| 2018/0040255 | A1 * | 2/2018 | Freeman ............... | A61H 31/02 |
| 2019/0105016 | A1 * | 4/2019 | Jenaro ................... | A61B 8/469 |
| 2021/0228177 | A1 * | 7/2021 | Sasaki ................... | A61B 8/488 |
| 2023/0132927 | A1 * | 5/2023 | Wen ....................... | A61B 8/465 |
| | | | | 600/437 |
| 2024/0115237 | A1 * | 4/2024 | Chamberlain ...... | G01S 7/52084 |
| 2024/0148367 | A1 * | 5/2024 | Samangouei ......... | G16H 30/40 |

FOREIGN PATENT DOCUMENTS

WO      WO-2013041992 A1 *   3/2013   ............. A61B 8/429

* cited by examiner

*Primary Examiner* — Alexei Bykhovski
(74) *Attorney, Agent, or Firm* — Womble Bond Dickinson
(US) LLP

(57)     ABSTRACT

Methods and ultrasound systems for generating ultrasound
protocols are disclosed. In some embodiments, the ultra-
sound system includes an ultrasound scanner configured to
transmit ultrasound at a patient anatomy and receive reflec-
tions of the ultrasound from the patient anatomy as part of
a current ultrasound examination that includes workflow
steps; an ultrasound machine configured to generate image
data based on the reflections and a configuration state of the
ultrasound machine; and a processor system. In some
embodiments, the ultrasound system is configured to record
protocol data including the configuration state and the
workflow steps, generate an ultrasound protocol based on
the protocol data, and store the ultrasound protocol in a
memory storage device for use in a subsequent ultrasound
examination.

20 Claims, 11 Drawing Sheets

100

200

300

500

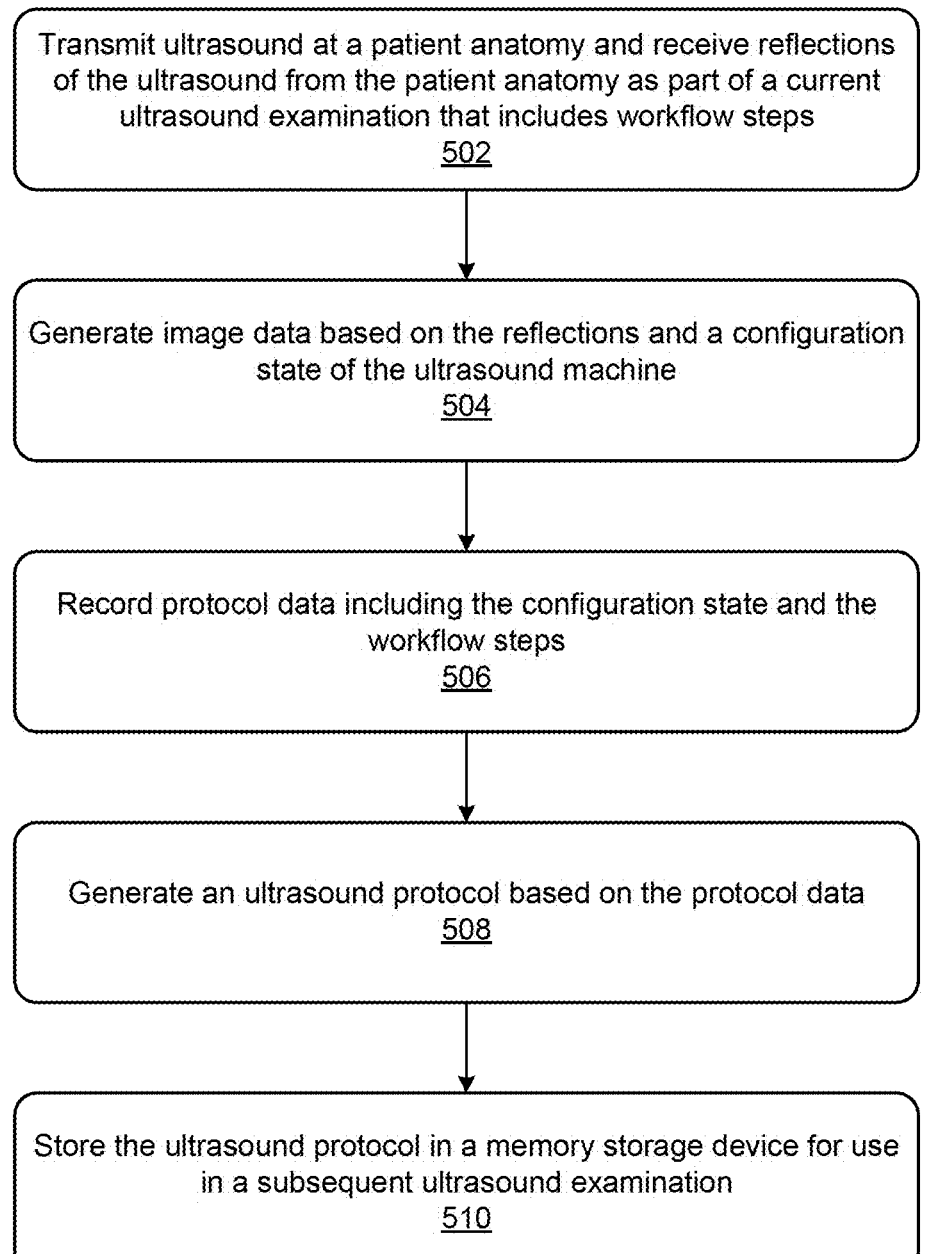

Transmit ultrasound at a patient anatomy and receive reflections
of the ultrasound from the patient anatomy as part of a current
ultrasound examination that includes workflow steps
502

Generate image data based on the reflections and a configuration
state of the ultrasound machine
504

Record protocol data including the configuration state and the
workflow steps
506

Generate an ultrasound protocol based on the protocol data
508

Store the ultrasound protocol in a memory storage device for use
in a subsequent ultrasound examination
510

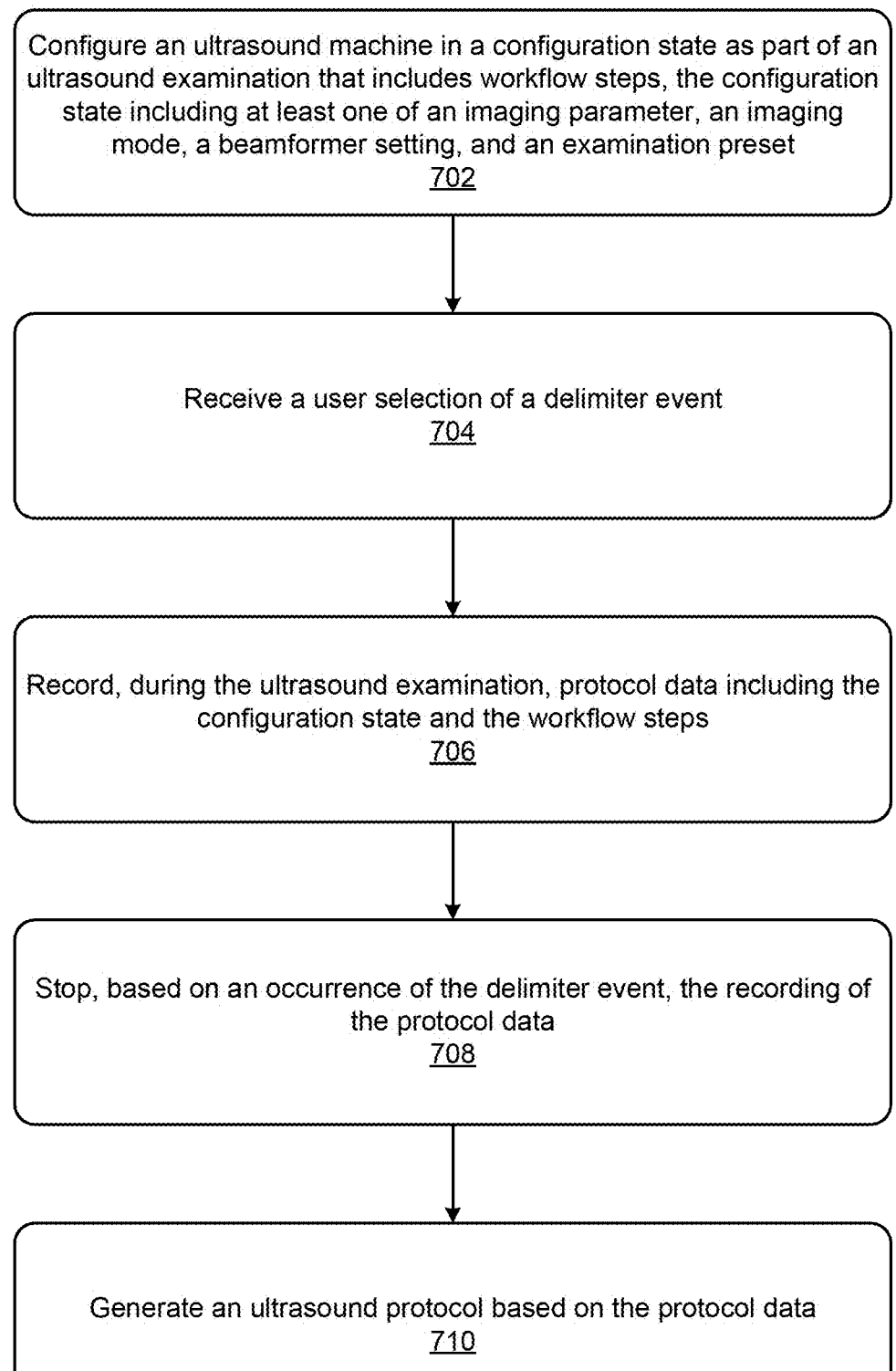

700

Configure an ultrasound machine in a configuration state as part of an ultrasound examination that includes workflow steps, the configuration state including at least one of an imaging parameter, an imaging mode, a beamformer setting, and an examination preset
702

Receive a user selection of a delimiter event
704

Record, during the ultrasound examination, protocol data including the configuration state and the workflow steps
706

Stop, based on an occurrence of the delimiter event, the recording of the protocol data
708

Generate an ultrasound protocol based on the protocol data
710

GENERATING ULTRASOUND PROTOCOLS

FIELD OF THE INVENTION

Embodiments disclosed herein relate to ultrasound systems. More specifically, embodiments disclosed herein are related to generating ultrasound protocols for use when performing examinations with an ultrasound system.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and non-ionizing, ultrasound systems are used ubiquitously, including at departments throughout a hospital or care facility, such as emergency departments, critical care departments, radiography departments, and the like. Usually, ultrasound protocols are designed for a department of a care facility and distributed to clinicians of the department.

However, the protocols often do not fit the clinicians' needs. For instance, the protocol may not include all of the steps needed for an examination. In some cases, a clinician may perform a step merely for protocol compliance, despite that the clinician thinks the step is unnecessary, resulting in inefficient use of the clinician's time. In other cases, the clinician may perform steps that are not part of the protocol. Hence, a protocol may not be consistent with the examinations that are actually performed in the care facility. As a result, protocol results (e.g., archived medical data) may be biased and/or contain incomplete data sets. Accordingly, patients may not receive the best care possible.

SUMMARY

Methods and ultrasound systems for generating ultrasound protocols are disclosed. In some embodiments, the ultrasound system includes an ultrasound scanner configured to transmit ultrasound at a patient anatomy and receive reflections of the ultrasound from the patient anatomy as part of a current ultrasound examination that includes workflow steps; an ultrasound machine configured to generate image data based on the reflections and a configuration state of the ultrasound machine; and a processor system. In some embodiments, the ultrasound system is configured to record protocol data including the configuration state and the workflow steps, generate an ultrasound protocol based on the protocol data, and store the ultrasound protocol in a memory storage device for use in a subsequent ultrasound examination.

In some embodiments, an ultrasound machine includes a display device configured to display a user interface that includes an ultrasound image generated as part of a current ultrasound examination performed using the ultrasound machine and an ultrasound protocol generated with the ultrasound machine based on workflow steps of the current ultrasound examination, the ultrasound image, and a configuration state of the ultrasound machine when the ultrasound image is generated. The user interface is configured to receive, during the current ultrasound examination, a user edit to the ultrasound protocol. In some embodiments, the ultrasound machine also includes a transceiver configured to transmit the ultrasound protocol to a protocol database for use in a subsequent ultrasound examination and receive from the protocol database an additional ultrasound protocol generated during a previous ultrasound examination.

In some other embodiments, an ultrasound system includes an ultrasound machine configured in a configuration state as part of an ultrasound examination that includes workflow steps, where the configuration state includes at least one of an imaging parameter, an imaging mode, a beamformer setting, and an examination preset. The ultrasound system also includes a processor system configured to: receive a user selection of a delimiter event; record, during the ultrasound examination, protocol data including the configuration state and the workflow steps; stop, based on an occurrence of the delimiter event, the recording of the protocol data; and generate an ultrasound protocol based on the protocol data.

BRIEF DESCRIPTION OF THE DRAWINGS

The appended drawings illustrate examples and are, therefore, exemplary embodiments and not considered to be limiting in scope.

FIG. 5 illustrates an example method that can be implemented by an ultrasound system in accordance with some embodiments.

FIG. 7 illustrates an example method that can be implemented by an ultrasound system in accordance with some embodiments.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Conventional ultrasound systems are used ubiquitously, including at various departments throughout a hospital or care facility, such as emergency departments, critical care departments, radiography departments, and the like. Usually, ultrasound protocols are designed for a department of a care facility and distributed to clinicians of the department. However, the protocols often do not fit the clinicians' needs. For instance, the protocol may not include all of the steps needed for an examination. In some cases, a clinician may perform a step merely for protocol compliance, despite that the clinician thinks the step is unnecessary, resulting in inefficient use of the clinician's time. In other cases, the clinician may perform steps that are not part of the protocol. Hence, a protocol may not be consistent with the examinations that are actually performed in the care facility. As a result, protocol results may be biased and/or contain incomplete data sets, and patients may not receive the best care possible.

Accordingly, systems, devices, and techniques are disclosed herein for generating ultrasound protocols during an ultrasound examination based on the configuration settings of an ultrasound machine and the workflow steps performed by an operator of the ultrasound machine. The ultrasound protocols can be stored on the ultrasound machine and/or sent to a database of protocols, so that they can be shared with other clinicians for repeated use as well as training. Hence, the systems, devices, and methods disclosed herein can be used to generate ultrasound protocols that necessarily match the clinician's needs and methods, and the protocol results are not biased due to forced participation with protocol steps. Further, the use of the ultrasound protocols generated with the systems, devices, and techniques disclosed herein result in efficient use of the clinician's time, and patients can receive better care than when conventional ultrasound systems and protocols are used.

An Example Ultrasound System

Figure 1:
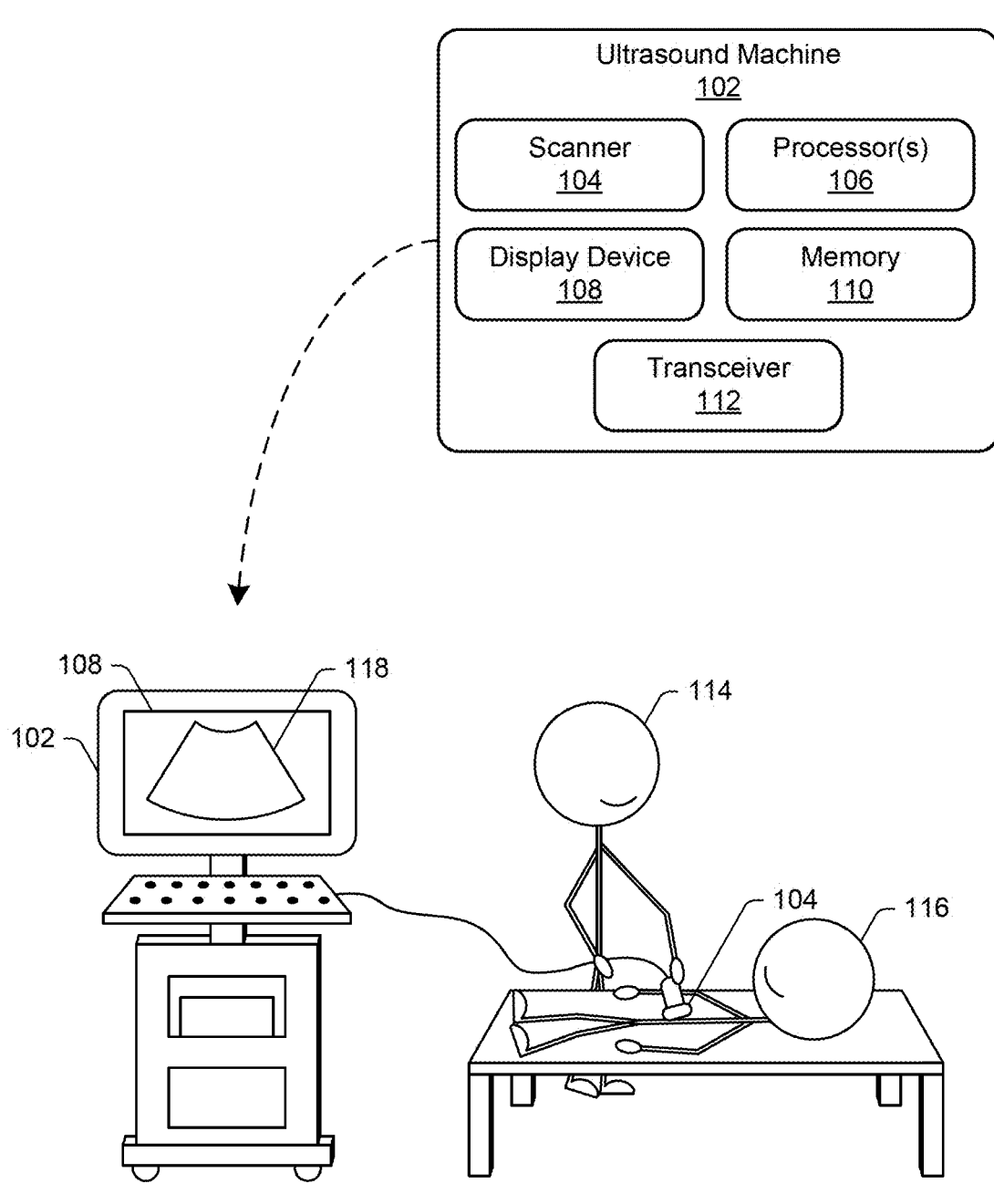
FIG. 1 illustrates an ultrasound system in an environment for generating ultrasound protocols during an ultrasound examination.

FIG. 1 illustrates some embodiments of an ultrasound system in an environment 100 for generating ultrasound protocols during an ultrasound examination. The ultrasound system includes an ultrasound machine 102 and an ultrasound scanner 104.

The ultrasound machine 102 generates high-frequency sound waves (e.g., ultrasound) and imaging data based on the ultrasound reflecting off a patient anatomy/body structure. The ultrasound machine 102 includes various components, some of which include the scanner 104, one or more processors 106, a display device 108, a memory 110, and a transceiver 112.

A user 114 (e.g., nurse, ultrasound technician, operator, sonographer, clinician, etc.) directs the scanner 104 toward a patient 116 to non-invasively scan internal bodily structures (e.g., patient anatomies such as organs, tissues, bones, etc.) of the patient 116 for testing, diagnostic, therapeutic, or procedural reasons. In some embodiments, the scanner 104 includes an ultrasound transducer array and electronics communicatively coupled to the ultrasound transducer array to transmit ultrasound signals to the patient's anatomy and receive ultrasound signals reflected from the patient's anatomy. In some embodiments, the scanner 104 is an ultrasound scanner, which can also be referred to as an ultrasound probe.

The display device 108 is coupled to the processor 106, which can include any suitable processor, number of processors, or processor system, such as one or more CPUs, GPUs, vector processors, RISC processors, CISC processors, VLIW processors, etc. The processor 106 can execute instructions stored on memory 110 to perform operations disclosed herein for generating ultrasound protocols. For example, the processor 106 can process the reflected ultrasound signals to generate ultrasound data, including an ultrasound image. The display device 108 is configured to generate and display an ultrasound image (e.g., ultrasound image 118) of the anatomy based on the ultrasound data generated by the processor 106 from the reflected ultrasound signals detected by the scanner 104. In some aspects, the ultrasound data includes the ultrasound image 118 or data representing the ultrasound image 118. The transceiver 112 is configured to transmit, e.g., over a network maintained by a care facility, an ultrasound protocol generated by the ultrasound system to a database of protocols (not shown in FIG. 1 for clarity), and receive additional protocols from the database of protocols for use on the ultrasound system illustrated in FIG. 1.

Figure 2:
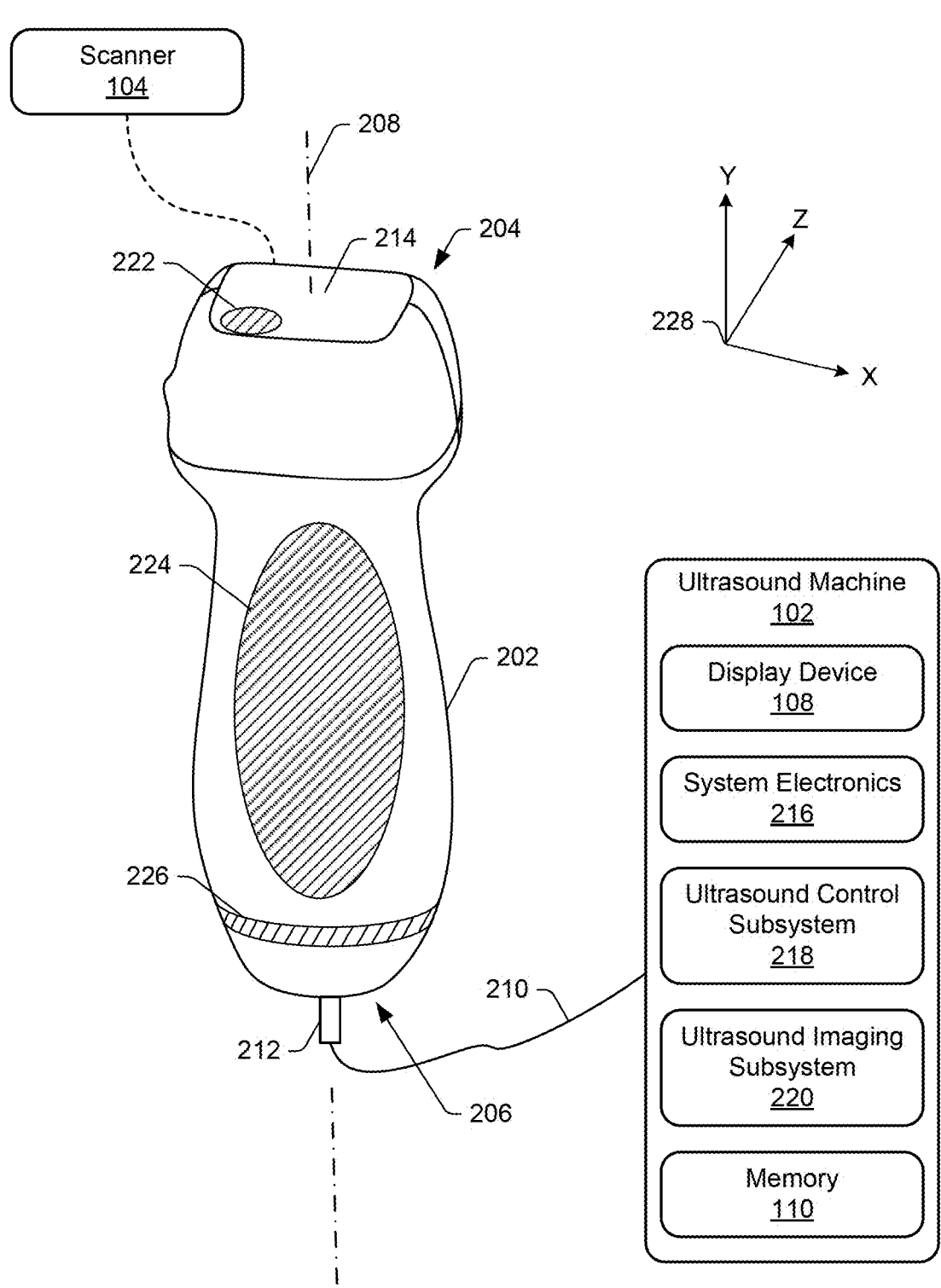
FIG. 2 illustrates an example implementation of the ultrasound system illustrated in the environment of FIG. 1.

FIG. 2 illustrates some embodiments of an example implementation 200 of the ultrasound system illustrated in the environment 100 of FIG. 1. In the implementation 200, the scanner 104 (e.g., ultrasound scanner) includes an enclosure 202 extending between a distal end portion 204 and a proximal end portion 206. The enclosure 202 includes a central axis 208 (e.g., longitudinal axis) that intersects the distal end portion 204 and the proximal end portion 206. The central axis 208 corresponds to an axial direction of the scanner 104. The scanner 104 is electrically coupled to an ultrasound imaging system (e.g., the ultrasound machine 102) via a coupling 210. In some embodiments, the coupling 210 includes a cable that is attached to the proximal end portion 206 of the scanner 104 by a strain-relief element 212. In some embodiments, the coupling 210 includes a wireless coupling so that the scanner 104 is wirelessly coupled to the ultrasound imaging system and communicates with the ultrasound imaging system via one or more wireless transmitters, receivers, or transceivers over a wireless connection or network (e.g., Bluetooth™, Wi-Fi™, etc.).

A transducer assembly 214 having one or more transducer elements is electrically coupled to system electronics 216 in the ultrasound machine 102. In operation, the transducer assembly 214 transmits ultrasound energy from the one or more transducer elements toward a subject (e.g., patient) and receives ultrasound echoes from the subject. The ultrasound echoes are converted into electrical signals by the transducer element(s) and electrically transmitted to the system electronics 216 in the ultrasound machine 102 for processing and generation of one or more ultrasound images.

Capturing ultrasound data from a subject using a transducer assembly (e.g., the transducer assembly 214) generally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 Megahertz (MHz)) and/or high-frequency ultrasound (e.g., greater than or equal to 15 MHz). A particular frequency range to use can readily be determined based on various factors, including, for example, depth of imaging, desired resolution, and so forth.

In some embodiments, the system electronics 216 include one or more processors (e.g., the processor(s) 106 from FIG. 1), integrated circuits, application-specific integrated circuits (ASICs), Field Programmable Gate Arrays (FPGAs), and power sources to support functioning of the ultrasound machine 102. In some embodiments, the ultrasound machine 102 also includes an ultrasound control subsystem 218 having one or more processors. At least one processor, FPGA, or ASIC can cause electrical signals to be transmitted to the transducer(s) of the scanner 104 to emit sound waves and also receive electrical pulses from the scanner 104 that were created from the returning echoes. One or more processors, FPGAs, or ASICs can process the raw data associated with the received electrical pulses and form an image that is sent to an ultrasound imaging subsystem 220, which causes the image (e.g., the image 118 in FIG. 1) to be displayed via the display device 108. Thus, the display device 108 displays ultrasound images from the ultrasound data processed by the processor(s) of the ultrasound control subsystem 218.

In some embodiments, the ultrasound machine 102 also includes one or more user input devices (e.g., a keyboard, a cursor control device, a microphone, a camera, touchscreen, etc.) that input data and enable taking measurements from the display device 108 of the ultrasound machine 102. The ultrasound machine 102 can also include a disk storage device (e.g., computer-readable storage media such as read-only memory (ROM), a Flash memory, a dynamic random-access memory (DRAM), a NOR memory, a static random-access memory (SRAM), a NAND memory, and so on) for storing the acquired ultrasound data. In some embodiments, the disk storage device includes the memory 110, which is local to the ultrasound machine 102. Alternatively, the memory 110 used for storing the acquisition data can be remote, such as on a remote server communicatively connected to the ultrasound machine 102. In addition, the ultrasound machine 102 can include a printer that prints the image from the displayed data. To avoid obscuring the techniques described herein, such user input devices, disk storage device, and printer are not shown in FIG. 2.

The ultrasound scanner 104 in the implementation 200 also includes one or more pressure sensors 222 on the lens of the scanner 104, and one or more pressure sensors 224 on the enclosure 202 of the scanner 104. The pressure sensors 222 and 224 can be included in, on, or under a sensor region any suitable type of sensors for determining a pressure. In some embodiments, the pressure sensors 222 and 224 include capacitive sensors that can measure a capacitance, or change in capacitance, caused by a user's touch or proximity of touch, as is common in touchscreen technologies. The pressure sensors 222 and 224 can generate sensor data indicative of a touch or pressure. The sensor data can include a binary indicator that indicates the presence and absence of a touch on the sensor. For instance, a "1" for sensor data can indicate that a pressure is sensed at the pressure sensor, and a "0" for the sensor data can indicate that a pressure is not sensed at the pressure sensor. Additionally or alternatively, the sensor data can include a multi-level indicator that indicates an amount of pressure on the sensor, such as an integer scale from zero to five. For instance, a "0" can indicate that no pressure is detected at the sensor, and a "1" can indicate a small amount of pressure is detected at the sensor. A "2" can indicate a larger amount of pressure is detected at the sensor than a "1", and a "5" can indicate a maximum amount of pressure is detected at the sensor.

The pressure sensors 222 and 224 are illustrated in FIG. 2 as ellipses for clarity, and generally can be of any suitable shape and size, and generate sensor data indicating pressure at any suitable number of points. For instance, in some embodiments, the pressure sensors 222 cover an exterior surface of the lens of the scanner 104 and are used to determine when the scanner is placed against a patient. Additionally or alternatively, the pressure sensors 224 can substantially cover the enclosure 202 of the scanner 104 and can used to determine when a clinician grabs the scanner 104 for use in an ultrasound examination. The ultrasound system can use the sensor data from one or both of the pressure sensors 222 and 224 as a delimiter event used to start and/or stop recording of protocol data for generating ultrasound protocols. As an example, in some embodiments, when both the pressure sensors 222 and 224 indicate pressure above a certain threshold for a threshold area size, the ultrasound system can start to record protocol data for generating an ultrasound protocol. Additionally or alternatively, in some embodiments, when the pressure sensors 222 indicate pressure below a certain threshold for a threshold area size, the ultrasound system can stop the recording of the protocol data for generating the ultrasound protocol. The protocol data can include any suitable data for generating an ultrasound protocol, including a configuration state of the ultrasound machine 102, workflow steps performed by the clinician during the ultrasound examination, ultrasound image data, and positional data of the scanner 104.

In some embodiments, the scanner 104 includes an inertial measurement unit (IMU) 226 for generating the positional data that determines a position and orientation of the scanner 104 in a coordinate system, e.g., the coordinate system 228 in FIG. 2. The IMU can include a combination of accelerometers, gyroscopes, and magnetometers, and generate positional data including data representing six degrees of freedom (6DOF), such as yaw, pitch, and roll angles in a coordinate system. Typically, 6DOF refers to the freedom of movement of a body in three-dimensional space. For example, the body is free to change position as forward/backward (surge), up/down (heave), left/right (sway) translation in three perpendicular axes, combined with changes in orientation through rotation about three perpendicular axes, often termed yaw (normal axis), pitch (transverse axis), and roll (longitudinal axis). Additionally or alternatively, the ultrasound system can include a camera and fiducial markers on the scanner 104 (not shown in FIG. 2) to determine the positional data for the ultrasound scanner 104.

Figure 3:
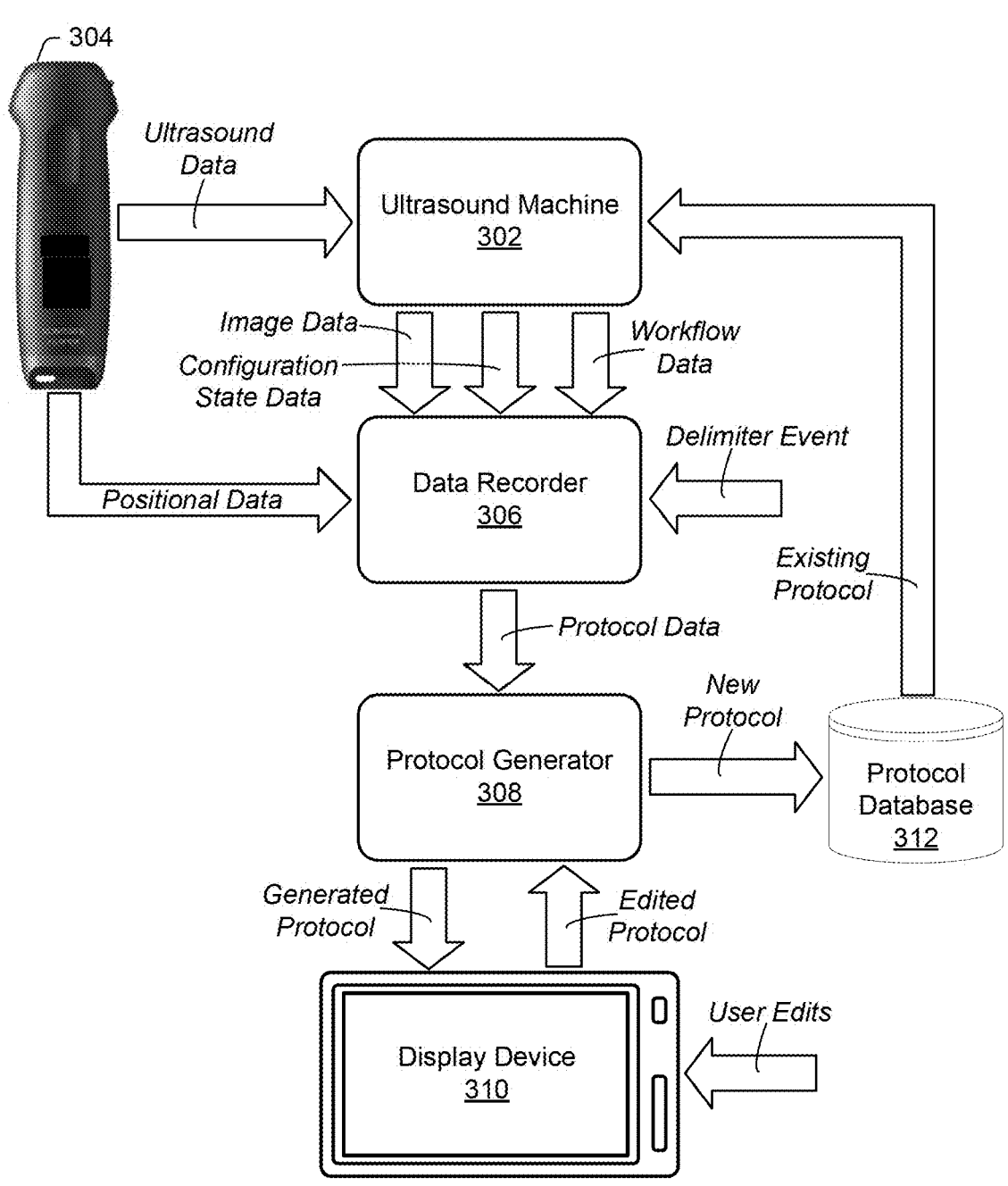
FIG. 3 illustrates an example ultrasound system for generating ultrasound protocols in accordance with some embodiments.

FIG. 3 illustrates an example ultrasound system 300 for generating ultrasound protocols in accordance with some embodiments. The ultrasound system 300 is an example of the ultrasound system illustrated in the environment of FIG. 1 and the implementation 200 in FIG. 2.

In FIG. 3, the ultrasound system 300 includes an ultrasound machine, which is an example of the ultrasound machine 102, and an ultrasound scanner 304, which is an example of the scanner 104. The ultrasound system 300 also includes a data recorder 306, a protocol generator 308, a display device 310, and a protocol database 312. The display device 310 is an example of the display device 108. In some embodiments, the protocol database 312 is implemented in the memory 110. Additionally or alternatively, the protocol database 312 can be implemented remote to the ultrasound system 300 and/or ultrasound machine 302, such as by a server or network-connected device (not shown in FIG. 3 for clarity).

The ultrasound scanner 304 generates ultrasound and directs it at a patient anatomy. Based on reflections of the ultrasound from the patient anatomy, the ultrasound scanner 304 generates ultrasound data (e.g., electrical signals representing the ultrasound reflections) and provides the ultrasound data to the ultrasound machine 302, such as via a cable and/or wireless communication link. The ultrasound scanner 304 also provides positional data to the data recorder 306. In some embodiments, the positional data indicates a location and orientation of the ultrasound scanner 304 in a coordinate system.

The ultrasound machine 302 generates image data from the ultrasound data and based on a configuration state of the ultrasound machine 302. The configuration state can include any suitable data that describes a configuration and/or state of the ultrasound machine 302, such as, for example, imaging parameters (e.g., depth, gain, etc.), an imaging mode (e.g., B-mode, M-Mode, Doppler, etc.), an examination preset, a beamformer configuration, and the like. The ultrasound machine 302 provides the image data and configuration state data to the data recorder 306. The ultrasound machine 302 also provides workflow data to the data recorder 306. The workflow data represents workflow steps and results of the steps performed by an operator of the ultrasound system 300 during an ultrasound examination. For instance, the workflow data can include annotations, measurements, and labels generated during the ultrasound examination, such as manually by the operator and/or automatically via a machine-learned model. The data sets provided by the ultrasound machine 302 to the data recorder 306 can include time stamps, to indicate relative orders of events during the ultrasound examination, so that the ultrasound system 300 can generate an ultrasound protocol from the data sets that accurately represents the steps and outcomes of the ultrasound examination.

The data recorder 306 receives the image data, configuration data, and workflow data from the ultrasound machine 302, and records these data sets as protocol data. In some embodiments, the protocol data includes a checklist of ultrasound images and/or actions a user performing an ultrasound examination is to take. The data recorder 306 also receives one or more delimiter events whose occurrence can instruct the data recorder 306 to start and/or stop recording the protocol data. In some embodiments, an indication of an occurrence of the delimiter event is based on pressure data from the ultrasound scanner 304. When the pressure of the scanner 304 against a patient exceeds a threshold amount or pressure, the data recorder can start to record the protocol data. Additionally or alternatively, a user can press a "record now" button or speak a "record now" voice command to indicate the occurrence of a delimiter event to instruct the data recorder 306 to start recording the protocol data. Hence, the delimiter event can be based on an action performed via the ultrasound machine 302 and/or the display device 310. A delimiter event can also be used by the data recorder 306 to stop the recording of the protocol data. For example, the action of recording or saving an image or video clip on the ultrasound machine 302 can serve as a delimiter event used by the data recorder 306 to stop recording the protocol data. In this way, the delimiter can be used to signal the user of the ultrasound machine 302 that is moving to perform the next or another part of a protocol.

In some embodiments, the occurrence of a delimiter event can be determined by a machine-learned model, such as a neural network. For example, the machine-learned model can determine a pause in the ultrasound examination and instruct the data recorder 306 to stop the recording of the protocol data. In some embodiments, the delimiter events are user defined, such as via a user interface displayed on the display device 310. For instance, in some embodiments, a user can designate a button or slider setting as a delimiter event. By toggling the button or slider, the user can instruct the data recorder 306 to start and stop the recording of the protocol data. In some embodiments, the user can select the saving of ultrasound data (e.g., an image or video clip) as a delimiter event whose occurrence instructs the data recorder 306 to stop the recording of the protocol data.

The data recorder 306 provides the protocol data to the protocol generator 308, which generates an ultrasound protocol based on the protocol data. The ultrasound protocol can include text, images, videos, animations, etc. that document the steps, settings, and outcomes of the ultrasound examination, so that the ultrasound examination is repeatable. In some embodiments, the ultrasound protocol is made repeatable by providing access to the recorded protocol data during a subsequent ultrasound examination. In some other embodiments, the ultrasound protocol is made repeatable by sending the ultrasound protocol to remote locations (e.g., other hospitals, clinics, and other medical facilities, medical schools, etc.) for use by individuals at those locations in subsequent ultrasound examinations.

In some embodiments, the protocol generator 308 generates image data that illustrates an expected view or desired image to be captured during the ultrasound examination as part of the ultrasound protocol. The image can be displayed concurrently with a protocol step to show assist the operator/clinician. The image can be generated in a desired style, by transferring the style of an ultrasound image generated during an ultrasound examination to the desired style. In some embodiments, the protocol generator 308 includes a machine-learned model implemented to generate an image in the style of another image, as described in U.S. Pat. No. 11,435,460 issued Sep. 6, 2022 to Dhatt and entitled Ultrasound Imaging System with Style Transfer Image Enhancement. In some embodiments, the image style can be user selected from among a database of images in various styles. In some embodiments, the user can upload an image to the ultrasound system 300 and transfer the style of an ultrasound image generated during an ultrasound examination to the style of the uploaded image. The image generated in this manner can be included as part of the protocol, to help illustrate a protocol step.

In some embodiments, the protocol generator 308 generates, based on the positional data included in the protocol data, an instructional image (e.g., an illustration), indicating how to hold the ultrasound scanner 304 to best capture an ultrasound image of a particular anatomy. The protocol generator 308 can include a machine-learned model implemented to generate the instructional image based on the positional data and an image of the ultrasound scanner. In some embodiments, the machine-learned model is programmed to generate the instructional image for left-hand operation or for right-hand operation. The ultrasound protocol generated by the protocol generator 308 can include the instructional image. In some embodiments, a step of an ultrasound protocol generated by the protocol generator 308 includes text describing the step, a first image generated in the style of another image to show the operator an expected view to capture during the protocol step, and an instructional image depicting how to hold and orient the scanner to obtain the expected view.

The protocol generator 308 provides the protocol in generates to the display device 310, which displays, in a user interface, the protocol generated by the protocol generator 308. The display device can receive a user edit to the protocol. For example, a clinician can change the order of steps, copy and paste text, select a style of an image to be included in the ultrasound protocol, etc., to edit the ultrasound protocol. Once edited, the protocol generator 308 provides the ultrasound protocol (e.g., as a new ultrasound protocol) to the protocol database 312. Thus, the protocol generator 308 allows ultrasound protocols generated previously by the protocol generator 308 to be changed to create a new ultrasound protocol (e.g., a new version of the previous protocol, etc.). The protocol database 312 maintains (e.g., stores and manages) ultrasound protocols, including ultrasound protocols generated with the ultrasound machine 302, as well as existing ultrasound protocols, e.g., ultrasound protocols that were generated with additional ultrasound machines and/or by additional users. The protocol database 312 can provide one or more of the existing ultrasound protocols to the ultrasound machine 302 for use with the ultrasound system 300. Hence, the system provides for the sharing of ultrasound protocols that have been generated on different ultrasound systems by different ultrasound operators.

Example User Interface

Figure 4:
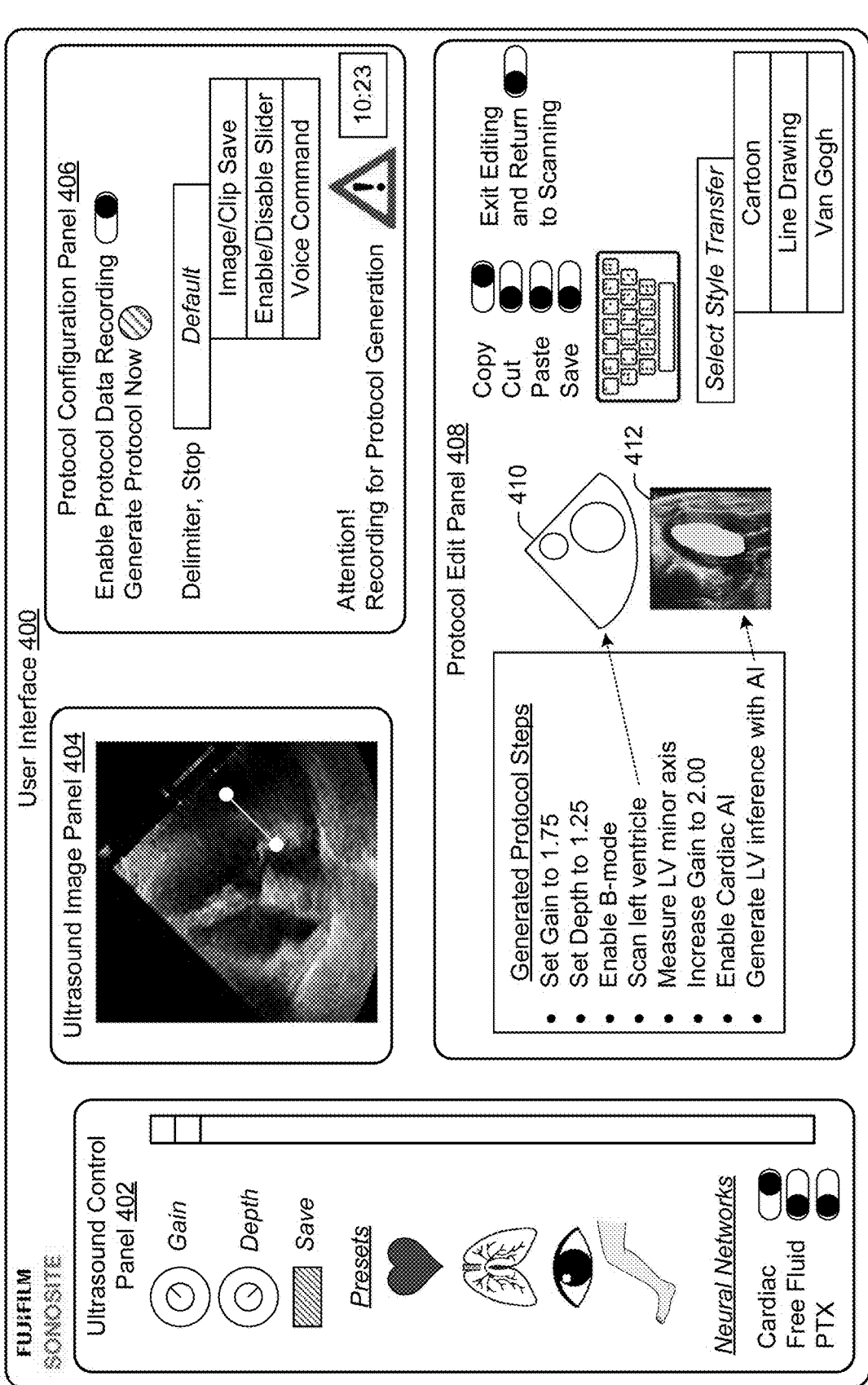
FIG. 4 illustrates an example user interface of an ultrasound system for generating ultrasound protocols in accordance with some embodiments.

FIG. 4 illustrates an example user interface 400 of an ultrasound system for generating ultrasound protocols in accordance with some embodiments. The user interface 400 can be displayed via an ultrasound machine (e.g., the ultrasound machine 102 or the ultrasound machine 302), and/or a display device (e.g., the display device 108 or the display device 310). In some embodiments, the user interface 400 includes an ultrasound control panel 402, an ultrasound image panel 404, a protocol configuration panel 406, and a protocol edit panel 408.

The ultrasound control panel 402 includes any suitable controls and settings for controlling an ultrasound system, such as, for example, but not limited to, depth and gain adjustments, and a button to store images and/or video clips. The ultrasound control panel 402 can also include icons to select examination presets, such as a heart icon for a cardiac preset, a lung icon for a respiratory preset, an eye icon for an ocular present, and a leg icon for a muscular-skeletal preset. The ultrasound control panel 402 can also include options to enable one or more neural networks for processing of an ultrasound image, such as an ultrasound image displayed in the ultrasound image panel 404. For instance, a cardiac neural network can be enabled to generate a value of ejection fraction, a free fluid network can be enabled to generate a segmentation of free fluid in an ultrasound image, and a pneumothorax (PTX) neural network can be enabled to generate a probability of a pneumothorax condition or collapsed lung. These controls are meant to be exemplary and nonlimiting.

The ultrasound image panel 404 can display any suitable ultrasound image, such as a B-mode image, M-mode image, Doppler image, etc. The ultrasound image panel 404 can also display a measurement, annotation, classification, and the like. For instance, a measurement including a line segment is illustrated in the ultrasound image panel 404 in FIG. 4. In some embodiments, the ultrasound image panel 404 can display an inference generated by a neural network, such as a segmentation of a patient anatomy.

The protocol configuration panel 406 can display any suitable data and selections for configuring the generation of ultrasound protocols. In the example in FIG. 4, the protocol configuration panel 406 includes a binary switch (e.g., with on and off positions) to enable and disable the recording of protocol data. In some embodiments, the protocol configuration panel 406 also includes a "generate protocol now" button to generate a protocol immediately upon pressing the button. In an example, pressing the "generate protocol now" button overrides the occurrence of a delimiter event and causes an ultrasound protocol to be generated without waiting for the occurrence of the delimiter event that may have been otherwise designated for protocol generation. For instance, in some embodiments, the protocol configuration panel 406 includes selections for delimiter events in a pull-down tab option, including a default delimiter event, the saving of an image or video clip, the user of a (binary) enable/disable slider, and a voice command. These delimiter events can be used by the system to stop recording of protocol data and commence the generation of an ultrasound protocol. The protocol configuration panel 406 can include selections for an additional delimiter event (not shown for clarity in FIG. 1), such as a delimiter event that is used by the system to start the recording of protocol data. The protocol configuration panel 406 can also display a warning to alert the operator that the system is currently recording protocol data. The warning in this example includes text and an icon. The warning includes a timer that indicates the time duration of the recording. In this example, protocol data for the generation of an ultrasound protocol has been recorded for 10 minutes and 23 seconds, illustrated by the 10:23 text box in the protocol configuration panel 406.

The protocol edit panel 408 displays an ultrasound protocol that has been generated by the system and facilitates the user editing of the generated protocol. In some embodiments, the user interface 400 displays the protocol edit panel 408 with the generated protocol responsive to the stopping of the recording of the protocol data. The protocol edit panel 408 displays the generated protocol steps in text, e.g., "set gain to 1.75; set depth to 1.25", etc. The protocol edit panel 408 also includes editing tools to edit the generated protocol, including copy, cut, and paste tools that can be selected and used to edit the text, including to re-order the steps of the ultrasound protocol. The protocol edit panel 408 also includes a keyboard tool, that when selected, enables a keyboard for insertion of text into an ultrasound protocol. The protocol edit panel 408 also includes a selection to save an ultrasound protocol, so that once a clinician has edited the ultrasound protocol to their satisfaction, the ultrasound protocol can be saved for sharing with other clinician and use in subsequent ultrasound examinations.

The ultrasound protocol generated by the system as part of a current ultrasound examination can include one or more images. For instance, the image 410 includes a line drawing depicting an expected view for the protocol step of "scan left ventricle", and the image 412 includes a segmentation image depicting an example segmentation of a left ventricle. In some embodiments, the style of the images included in the protocol edit panel 408 can be user selected. Accordingly, the protocol edit panel 408 includes a pull-down tab for selection of image style-transfer type, including image styles of cartoon, line drawing, and Van Gogh. As discussed previously, a user can select an image, such as an ultrasound image depicted in the ultrasound image panel 404 or a saved image, select an image style via the pull-down tabs, and enable a machine-learned model to transfer the style of the image to the selected style. The user can then add the image to the ultrasound protocol or replace an existing image already displayed in the ultrasound protocol.

In some embodiments, the system suspends scanning operation when the protocol edit panel 408 is displayed and/or editing of an ultrasound protocol is enabled. Suspending scanning can include reducing or disabling power to one or more components, e.g., an ultrasound scanner. In some embodiments, suspending scanning includes disabling transmission and reception of ultrasound from and by the ultrasound scanner. Hence, in some embodiments, the protocol edit panel 408 includes an input (e.g., switch or button) to exit the editing of the ultrasound protocol and resume scanning. When this input is selected and scanning is resumed, power can be restored to the ultrasound scanner so that it can transmit and receive ultrasound.

Example Procedures

Figure 10:
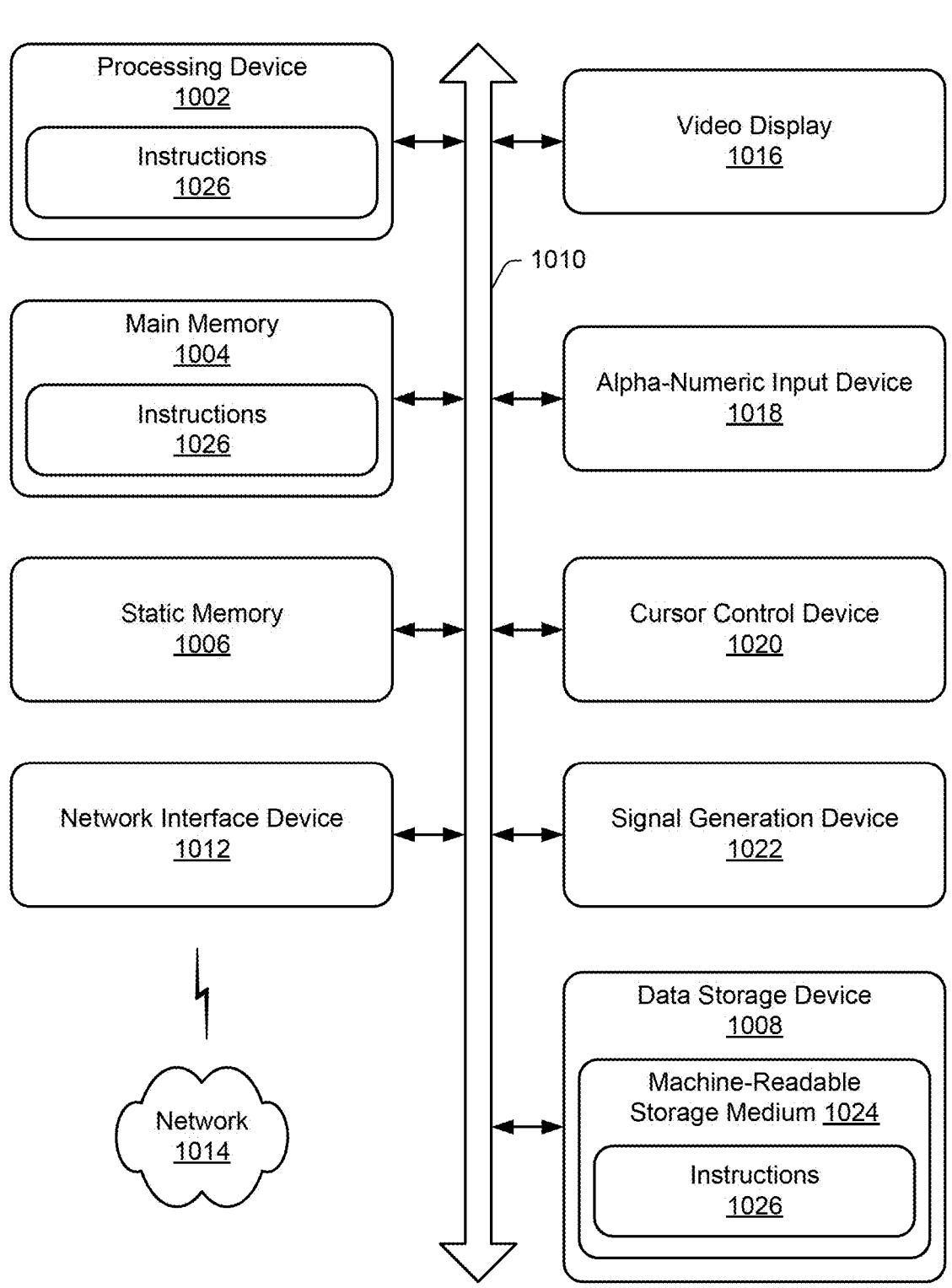
FIG. 10 illustrates a block diagram of an example computing device that can perform one or more of the operations described herein, in accordance with some implementations.

FIG. 5 illustrates an example method 500 that can be implemented by an ultrasound system in accordance with some embodiments. The ultrasound system can include an ultrasound scanner, an ultrasound machine, a processor system, a display device, and a transceiver. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 10.

Referring to FIG. 5, ultrasound is transmitted at a patient anatomy and reflections of the ultrasound from the patient anatomy are received as part of a current ultrasound examination that includes workflow steps (block 502). Image data is generated based on the reflections and a configuration state of the ultrasound machine (block 504). Protocol data including the configuration state and the workflow steps is recorded (block 506). An ultrasound protocol is generated based on the protocol data (block 508). The ultrasound protocol is stored in a memory storage device for use in a subsequent ultrasound examination (block 510).

In an example, the workflow steps include to generate a measurement of the patient anatomy based on the image data, and the ultrasound protocol includes instructions to generate the measurement. Additionally or alternatively, the workflow steps can include to generate an annotation for the patient anatomy based on the image data, and the ultrasound protocol can include instructions to generate the annotation.

In some embodiments, the ultrasound scanner includes an inertial measurement unit, and the protocol data includes positional data from the inertial measurement unit. The positional data can indicate an orientation and/or location of the ultrasound scanner with respect to a coordinate system. The ultrasound protocol can include instructions for placement of the ultrasound scanner based on the positional data. Additionally or alternatively, the ultrasound protocol can include holding instructions for holding the ultrasound scanner based on the positional data. The holding instructions can be user-selectable for left-handed or right-handed grip of the ultrasound scanner.

In some embodiments, the protocol data includes the image data, and the ultrasound protocol includes an ultrasound image generated based on the image data. The processor system can generate, based on the image data, an image in a non-ultrasound style, and the ultrasound protocol can include a display of the image in the non-ultrasound style. The non-ultrasound style can include at least one of an illustration, a cartoon, and a painting. The processor can implement a machine-learned model that transfers the image data from an ultrasound style to the non-ultrasound style to generate the image.

In some embodiments, the processor system determines an occurrence of a delimiter event during the current ultrasound examination, and stops the recording of the protocol data based on the occurrence of the delimiter event. The delimiter event can include to save the image data. For instance, once the image data is saved, the processor system stops the recording of the protocol data. In some embodiments, the processor implements a machine-learned model to determine the occurrence of the delimiter event.

In some embodiments, the ultrasound scanner includes a pressure sensor, and the processor system starts the recording of the protocol data based on pressure data from the pressure sensor. For example, the pressure data for an amount of area on a lens of the ultrasound scanner can exceed a threshold pressure amount, and thus indicate that the ultrasound scanner is placed against a patient, and this the processor system can start the recording of the protocol data.

In some embodiments, the ultrasound system includes a display device implemented to display the ultrasound protocol, and receive a user edit to the ultrasound protocol. The display device can receive a user instruction to stop editing the ultrasound protocol, and return, responsive to the user instruction, the ultrasound system to a scanning state for scanning of the patient anatomy, the scanning state being disabled while the editing of the ultrasound protocol is enabled. The display device can display an alert indicating the recording of the protocol data (e.g., when the recording is active/enabled).

Figure 6:
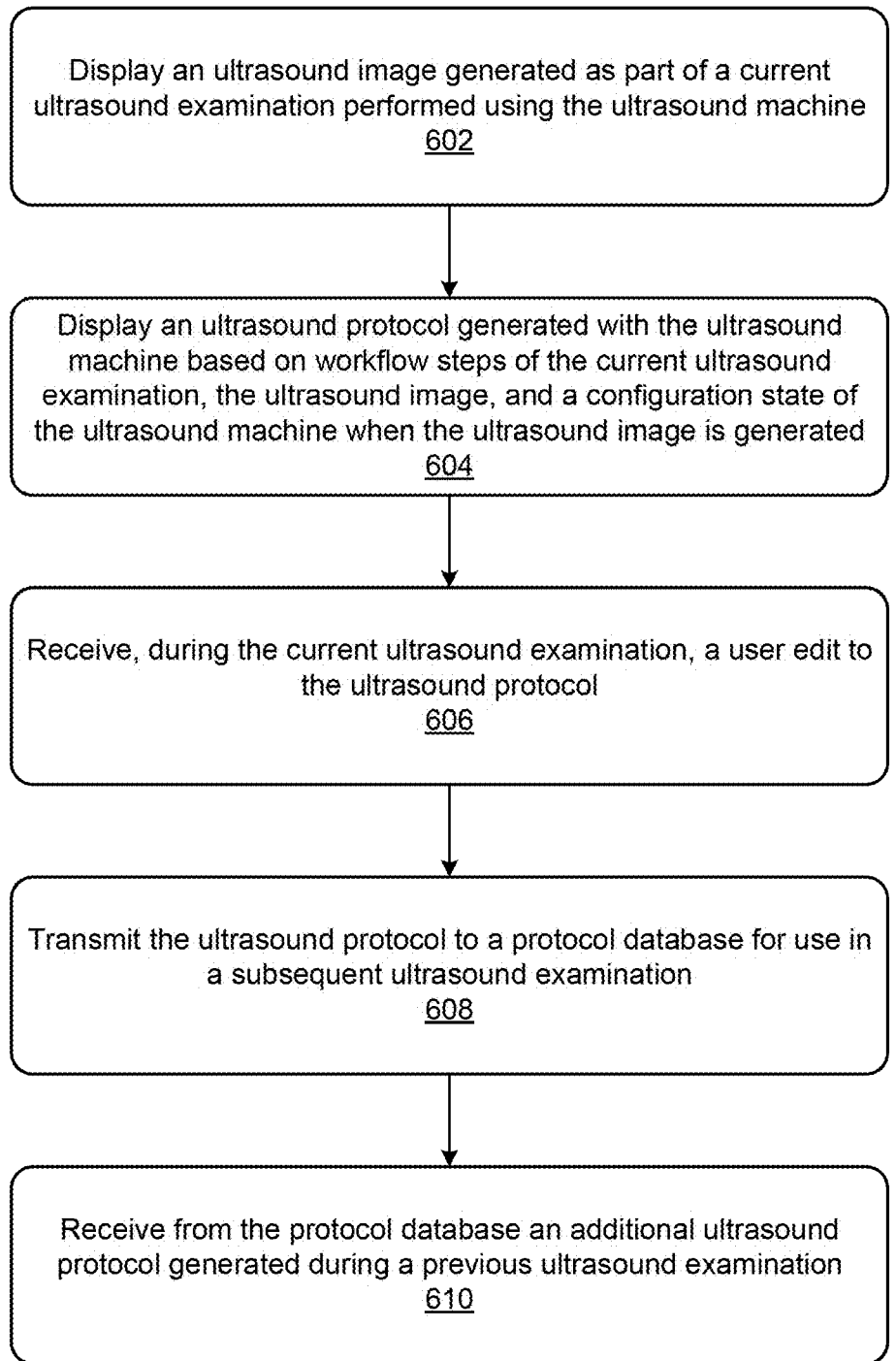
FIG. 6 illustrates an example method that can be implemented by an ultrasound system in accordance with some embodiments.

FIG. 6 illustrates an example method 600 that can be implemented by an ultrasound system in accordance with some embodiments. The ultrasound system can include an ultrasound scanner, an ultrasound machine, a processor system, a display device, and a transceiver. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 10.

Referring to FIG. 6, an ultrasound image is displayed that is generated as part of a current ultrasound examination performed using an ultrasound machine (block 602). An ultrasound protocol is displayed (block 604). In some embodiments, the ultrasound protocol is generated with the ultrasound machine based on workflow steps of the current ultrasound examination, the ultrasound image, and a configuration state of the ultrasound machine when the ultrasound image is generated. The configuration state of the ultrasound machine can include at least one of an imaging parameter, an imaging mode, a beamformer setting, and an examination preset. A user edit to the ultrasound protocol is received during the current ultrasound examination (block 606). The ultrasound protocol is transmitted to a protocol database for use in a subsequent ultrasound examination (block 608). An additional ultrasound protocol generated during a previous ultrasound examination is received from the protocol database (block 610).

In some embodiments, the transceiver transmits the ultrasound protocol to the protocol database for use in the subsequent ultrasound examination with an additional ultrasound machine. For example, the subsequent ultrasound examination can be performed using an additional ultrasound machine. Additionally or alternatively, the transceiver can receive the additional ultrasound protocol generated during the previous ultrasound examination by an additional ultrasound machine. For example, the previous ultrasound examination can be performed by an additional ultrasound machine that is used to generate the additional ultrasound protocol.

FIG. 7 illustrates an example method 700 that can be implemented by an ultrasound system in accordance with some embodiments. The ultrasound system can include an ultrasound scanner, an ultrasound machine, a processor system, a display device, and a transceiver. In some embodiments, the ultrasound system includes a computing device having processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem. In some embodiments, the computing device is represented by a computing device as shown in FIG. 10.

An ultrasound machine is configured in a configuration state as part of an ultrasound examination that includes workflow steps, where the configuration state includes at least one of an imaging parameter, an imaging mode, a beamformer setting, and an examination preset (block 702). A user selection of a delimiter event is received (block 704). Protocol data including the configuration state and the workflow steps is recorded during the ultrasound examination (block 706). The recording of the protocol data is stopped based on an occurrence of the delimiter event (block 708). An ultrasound protocol is generated based on the protocol data (block 710).

The systems, devices, and methods disclosed herein constitute numerous advantages over conventional systems, devices, and methods for generating ultrasound protocols. Hence, the systems, devices, and methods disclosed herein can be used to generate ultrasound protocols that necessarily match the clinician's needs and methods, and the protocol results are not biased due to forced participation with protocol steps. The protocols can be shared amongst clinicians for repeatability as well as training. Such usage can help define a standard of care for a particular ultrasound examination, which can create consistent outputs among clinicians. Further, the use of the ultrasound protocols generated with the systems, devices, and techniques disclosed herein result in efficient use of the clinician's time, and patients can receive better care than when conventional ultrasound systems and protocols are used.

Example Machine-Learned Model

Many of the aspects described herein can be implemented using a machine-learned model. For the purposes of this disclosure, a machine-learned model is any model that accepts an input, analyzes and/or processes the input based on an algorithm derived via machine-learning training, and provides an output. A machine-learned model can be conceptualized as a mathematical function of the following form:

$$f(\hat{s}, \theta) = \hat{y} \qquad \text{Equation (1)}$$

In Equation (1), the operator f represents the processing of the machine-learned model based on an input and providing an output. The term $\hat{s}$ represents a model input, such as ultrasound data. The model analyzes/processes the input s using parameters $\theta$ to generate output $\hat{y}$ (e.g., object identification, object segmentation, object classification, etc.). Both $\hat{s}$ and $\hat{y}$ can be scalar values, matrices, vectors, or mathematical representations of phenomena such as categories, classifications, image characteristics, the images themselves, text, labels, or the like. The parameters $\theta$ can be any suitable mathematical operations, including but not limited to applications of weights and biases, filter coefficients, summations or other aggregations of data inputs, distribution parameters such as mean and variance in a Gaussian distribution, linear algebra-based operators, or other parameters, including combinations of different parameters, suitable to map data to a desired output.

Figure 8:
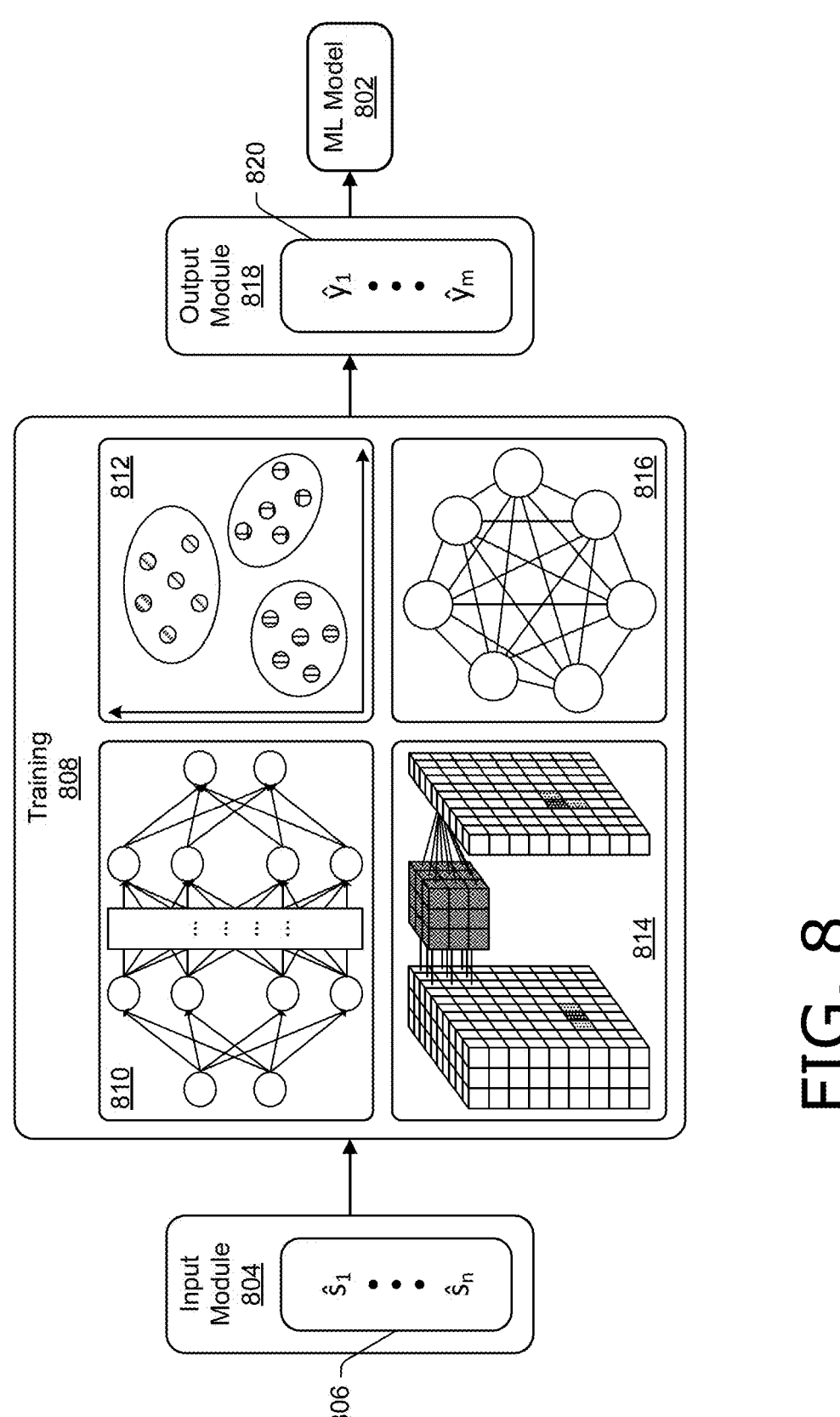
FIG. 8 represents an example machine-learning architecture used to train a machine-learned model.

FIG. 8 represents an example machine-learning architecture 800 used to train a machine-learned model 802. An input module 804 accepts an input $\hat{s}$ 806, which can be an array with members $\hat{s}_1$ through $\hat{s}_n$. The input $\hat{s}$ 806 is fed into a training module 808, which processes the input $\hat{s}$ 806 based on the machine-learning architecture 800. For example, if the machine-learning architecture 800 uses a multilayer perceptron (MLP) model 810, the training module 808 applies weights and biases to the input $806 through one or more layers of perceptrons, each perceptron performing a fit using its own weights and biases according to its given functional form. MLP weights and biases can be adjusted so that they are optimized against a least mean square, logcosh, or other optimization function (e.g., loss function) known in the art. Although an MLP model 810 is described here as an example, any suitable machine-learning technique can be employed, some examples of which include but are not limited to k-means clustering 812, convolutional neural networks (CNN) 814, a Boltzmann machine 816, Gaussian mixture models (GMM), and long short-term memory (LSTM). The training module 808 provides an input to an output module 818. The output module 818 analyzes the input from the training module 808 and provides an output in the form of $\hat{y}$ 820, which can be an array with members $\hat{y}_1$ through $\hat{y}_m$. The output $\hat{y}$ 820 can represent a known correlation with the input $\hat{s}$ 806, such as, for example, object identification, segmentation, and/or classification.

In some examples, the input $\hat{s}$ 806 can be a training input labeled with known output correlation values, and these known values can be used to optimize the output $\hat{s}$ 820 in training against the optimization/loss function. In other examples, the machine-learning architecture 800 can categorize the output $\hat{s}$ 820 values without being given known correlation values to the inputs $\hat{s}$ 806. In some examples, the machine-learning architecture 800 can be a combination of machine-learning architectures. By way of example, a first network can use the input $\hat{s}$ 806 and provide the output $\hat{s}$ 820 as an input SML to a second machine-learned architecture, with the second machine-learned architecture providing a final output $\hat{y}_f$. In another example, one or more machine-learning architectures can be implemented at various points throughout the training module 808.

In some machine-learned models, all layers of the model are fully connected. For example, all perceptrons in an MLP model act on every member of $\hat{s}$. For an MLP model with a 100×100 pixel image as the input, each perceptron provides weights/biases for 10,000 inputs. With a large, densely layered model, this may result in slower processing and/or issues with vanishing and/or exploding gradients. A CNN, which may not be a fully connected model, can process the same image using 5×5 tiled regions, requiring only 25 perceptrons with shared weights, giving much greater efficiency than the fully connected MLP model.

Figure 9:
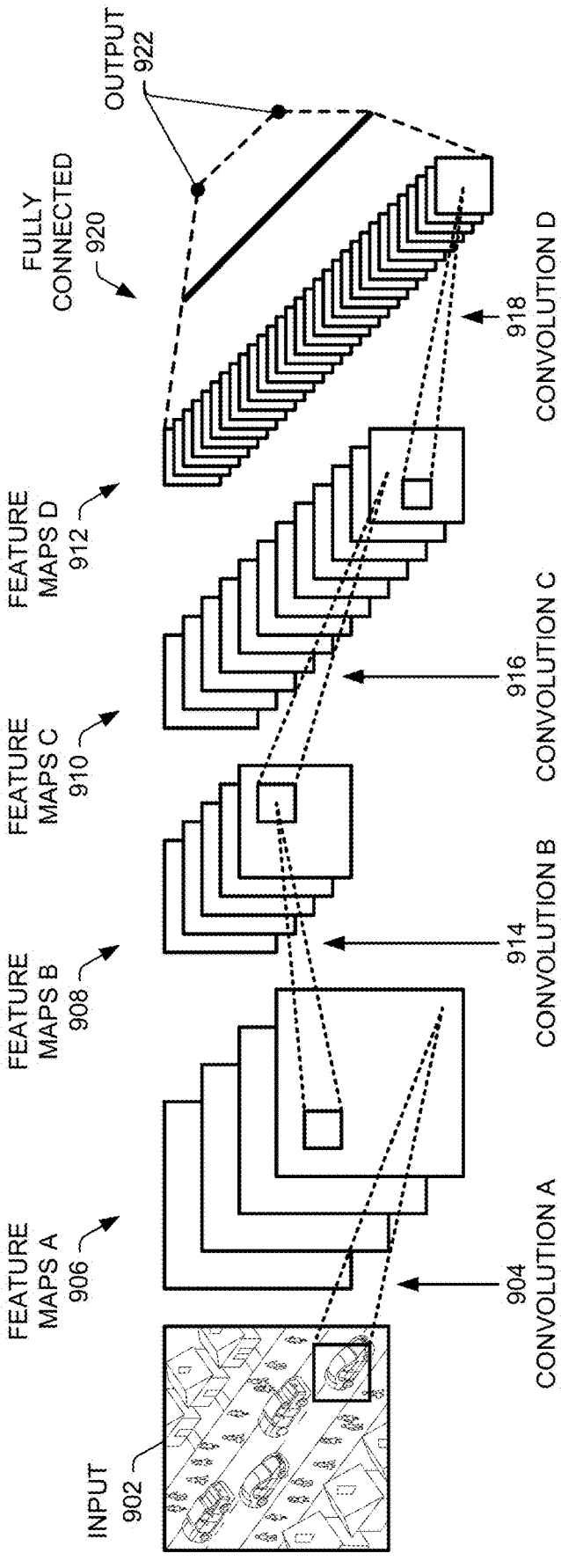
FIG. 9 represents an example model using a convolutional neural network (CNN) to process an input image, which includes representations of objects that can be identified via object recognition.

FIG. 9 represents some embodiments of an example model 900 using a CNN to process an input image 902, which includes representations of objects that can be identified via object recognition, such as people or cars (or an anatomy, as described in relation to FIGS. 1-8). Convolution A 904 can be performed to create a first set of feature maps (e.g., feature maps A 906). A feature map can be a mapping of aspects of the input image 902 given by a filter element of the CNN. This process can be repeated using feature maps A 906 to generate further feature maps B 908, feature maps C 910, and feature maps D 912 using convolution B 914, convolution C 916, and convolution D 918, respectively. In this example, the feature maps D 912 become an input for fully connected network layers 920. In this way, the machine-learned model can be trained to recognize certain elements of the image, such as people, cars, or a particular patient anatomy, and provide an output 922 that, for example, identifies the recognized elements. In some aspects, an inference generated with an ultrasound system can be appended to a feature map (e.g., feature map B 908) generated by a neural network (e.g., CNN). In this way, the feature vector and/or inference can be used as a secondary/conditional input to the neural network.

Although the example of FIG. 9 shows a CNN as a part of a fully connected network, other architectures are possible and this example should not be seen as limiting. There can be more or fewer layers in the CNN. A CNN component for a model can be placed in a different order, or the model can contain additional components or models. There may be no fully connected components, such as a fully convolutional network. Additional aspects of the CNN, such as pooling, downsampling, upsampling, or other aspects known to people skilled in the art can also be employed.

An Example Device

FIG. 10 illustrates a block diagram of some embodiments of a computing device 1000 that can perform one or more of the operations described herein. The computing device 1000 can be connected to other computing devices in a local area network (LAN), an intranet, an extranet, and/or the Internet. The computing device can operate in the capacity of a server machine in a client-server network environment or in the capacity of a client in a peer-to-peer network environment. The computing device can be provided by a personal computer (PC), a server computer, a desktop computer, a laptop computer, a tablet computer, a smartphone, an ultrasound machine, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some embodiments, the computing device 1000 is one or more of an ultrasound machine, an ultrasound scanner, an access point, and a packet-forwarding component.

The example computing device 1000 can include a processing device 1002 (e.g., a general-purpose processor, a programmable logic device (PLD), etc.), a main memory 1004 (e.g., synchronous dynamic random-access memory (DRAM), read-only memory (ROM), etc.), and a static memory 1006 (e.g., flash memory, a data storage device 1008, etc.), which can communicate with each other via a bus 1010. The processing device 1002 can be provided by one or more general-purpose processing devices such as a microprocessor, a central processing unit, or the like. In some embodiments, the processing device 1002 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 1002 can also comprise one or more special-purpose processing devices such as an application-specific integrated circuit (ASIC), a field programmable gate array (FPGA), a digital signal processor (DSP), a network processor, or the like. The processing device 1002 can be configured to execute the operations described herein, in accordance with one or more aspects of the present disclosure, for performing the operations and steps discussed herein.

The computing device 1000 can further include a network interface device 1012, which can communicate with a network 1014. The computing device 1000 also can include a video display unit 1016 (e.g., a liquid crystal display (LCD), an organic light-emitting diode (OLED), a cathode ray tube (CRT), etc.), an alphanumeric input device 1018 (e.g., a keyboard), a cursor control device 1020 (e.g., a mouse), and an acoustic signal generation device 1022 (e.g., a speaker, a microphone, etc.). In one embodiment, the video display unit 1016, the alphanumeric input device 1018, and the cursor control device 1020 can be combined into a single component or device (e.g., an LCD touch screen).

The data storage device 1008 can include a computer-readable storage medium 1024 on which can be stored one or more sets of instructions 1026 (e.g., instructions for carrying out the operations described herein, in accordance with one or more aspects of the present disclosure). The instructions 1026 can also reside, completely or at least partially, within the main memory 1004 and/or within the processing device 1002 during execution thereof by the computing device 1000, where the main memory 1004 and the processing device 1002 also constitute computer-readable media. The instructions can further be transmitted or received over the network 1014 via the network interface device 1012.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein are embodied in the data storage device 1008 of the computing device 1000 as executable instructions or code. Although represented as software implementations, the described modules can be implemented as any form of a control application, software application, signal-processing and control module, hardware, or firmware installed on the computing device 1000.

While the computer-readable storage medium 1024 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

An Example Environment

Figure 11:
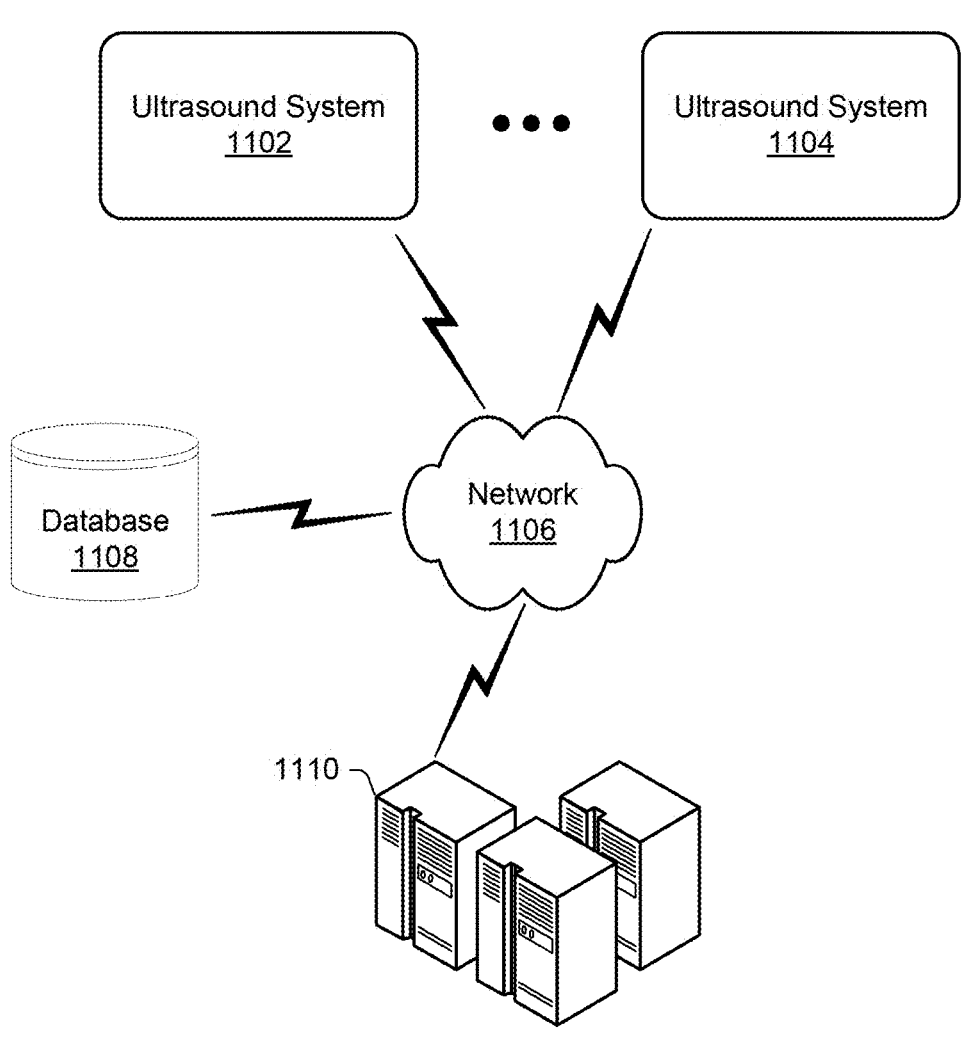
FIG. 11 illustrates an environment for an ultrasound system in accordance with some embodiments.

FIG. 11 illustrates an environment 1100 for an ultrasound system in accordance with some embodiments. The environment 1100 includes an ultrasound system 1102 and an ultrasound system 1104. Two example ultrasound systems 1102 and 1104 are illustrated in FIG. 11 for clarity. However, the environment 1100 can include any suitable number of ultrasound systems, such as the ultrasound systems maintained by a care facility or the department of a care facility. Generally, an ultrasound system can include any suitable device (e.g., a component of an ultrasound system). Examples devices of the ultrasound systems 1102 and 1104 include a charging station, an ultrasound machine, a display device (e.g., a tablet or smartphone), an ultrasound scanner, and an ultrasound cart. Other examples include a transducer cable, a transducer cable holder, a docking station for an ultrasound machine, a scanner station configured to hold one or more ultrasound scanners, a needle guide, a battery for a wireless ultrasound scanner, a battery for an ultrasound machine, a registration system, and the like.

The ultrasound systems 1102 and 1104 can be in communication via the network 1106 as part of the environment 1100. The network 1106 can include any suitable network, such as a local area network, a wide area network, a near field communication network, the Internet, an intranet, an extranet, a system bus that couples devices or device components (e.g., in an ASIC, FPGA, or SOC), and combinations thereof. Accordingly, in embodiments, information can be communicated to the ultrasound systems 1102 and 1104 through the network 1106. For instance, the database 1108 can store instructions executable by a processor system of the ultrasound systems 1102 and 1104, and communicate the instructions via the network 1106. The database 1108 can store ultrasound protocols and share them with the ultrasound systems 1102 and 1104.

In some embodiments, the environment 1100 also includes a server system 1110 that can implement any of the functions described herein. The server system 1110 can be a separate device from the ultrasound systems 1102 and 1104. Alternatively, the server system 1110 can be included in at least one of the ultrasound systems 1102 and 1104. In some embodiments, the server system 1110 and the database 1108 are included in at least one of the ultrasound systems 1102 and 1104. In some embodiments, the server system 1110 is implemented as a remote server system that is remote from (e.g., not collocated with) the ultrasound systems 1102 and 1104. Such remote availability can allow clinicians to access the ultrasound protocols they created at one location at other locations at which they perform.

There are a number of example embodiments described herein.

Example 1 is an ultrasound system comprising: an ultrasound scanner configured to transmit ultrasound at a patient anatomy and receive reflections of the ultrasound from the patient anatomy as part of a current ultrasound examination that includes workflow steps; an ultrasound machine configured to generate image data based on the reflections and a configuration state of the ultrasound machine; and a processor system. The process system is configured to: record protocol data including the configuration state and the workflow steps; generate an ultrasound protocol based on the protocol data; and store the ultrasound protocol in a memory storage device for use in a subsequent ultrasound examination.

Example 2 is the ultrasound system of example 1 that may optionally include that the workflow steps include to generate a measurement of the patient anatomy based on the image data, and the ultrasound protocol includes instructions to generate the measurement.

Example 3 is the ultrasound system of example 1 that may optionally include that the workflow steps include to generate an annotation for the patient anatomy based on the image data, and the ultrasound protocol includes instructions to generate the annotation.

Example 4 is the ultrasound system of example 1 that may optionally include that the ultrasound scanner includes an inertial measurement unit, the protocol data includes positional data from the inertial measurement unit, and the ultrasound protocol includes instructions for placement of the ultrasound scanner based on the positional data.

Example 5 is the ultrasound system of example 1 that may optionally include that the protocol data includes the image data, and the ultrasound protocol includes an ultrasound image generated based on the image data.

Example 6 is the ultrasound system of example 1 that may optionally include that the processor system is implemented to generate, based on the image data, an image in a non-ultrasound style, and the ultrasound protocol includes display of the image in the non-ultrasound style.

Example 7 is the ultrasound system of example 6 that may optionally include that the non-ultrasound style includes at least one of an illustration, a cartoon, and a painting.

Example 8 is the ultrasound system of example 6 that may optionally include that the processor is configured to implement a machine-learned model that transfers the image data from an ultrasound style to the non-ultrasound style to generate the image.

Example 9 is the ultrasound system of example 1 that may optionally include that the processor system is implemented to: determine an occurrence of a delimiter event during the current ultrasound examination; and stop the record of the protocol data based on the occurrence of the delimiter event.

Example 10 is the ultrasound system of example 9 that may optionally include that the delimiter event includes to save the image data.

Example 11 is the ultrasound system of example 9 that may optionally include that the processor is configured to implement a machine-learned model to determine the occurrence of the delimiter event.

Example 12 is the ultrasound system of example 1 that may optionally include that the ultrasound scanner includes a pressure sensor, and the processor system is implemented to start the record of the protocol data based on pressure data from the pressure sensor.

Example 13 is the ultrasound system of example 1 that may optionally include a display device implemented to: display the ultrasound protocol; and receive a user edit to the ultrasound protocol.

Example 14 is the ultrasound system of example 13 that may optionally include that the display device is implemented to: receive a user instruction to stop editing the ultrasound protocol; and return, responsive to the user instruction, the ultrasound system to a scanning state for scanning of the patient anatomy, the scanning state being disabled while the editing of the ultrasound protocol is enabled.

Example 15 is the ultrasound system of example 1 that may optionally include a display device implemented to display an alert indicating the recording of the protocol data.

Example 16 is an ultrasound machine comprising: a display device configured to display a user interface that includes: an ultrasound image generated as part of a current ultrasound examination performed using the ultrasound machine; and an ultrasound protocol generated with the ultrasound machine based on workflow steps of the current ultrasound examination, the ultrasound image, and a configuration state of the ultrasound machine when the ultrasound image is generated, where the user interface is configured to receive, during the current ultrasound examination, a user edit to the ultrasound protocol. The ultrasound machine also includes a transceiver configured to transmit the ultrasound protocol to a protocol database for use in a subsequent ultrasound examination and receive from the protocol database an additional ultrasound protocol generated during a previous ultrasound examination.

Example 17 is the ultrasound machine of example 16 that may optionally include that the transceiver is implemented to transmit the ultrasound protocol to the protocol database for use in the subsequent ultrasound examination with an additional ultrasound machine.

Example 18 is the ultrasound machine of example 16 that may optionally include that the transceiver is implemented to receive the additional ultrasound protocol generated during the previous ultrasound examination by an additional ultrasound machine.

Example 19 is the ultrasound machine of example 16 that may optionally include that the configuration state of the ultrasound machine includes at least one of an imaging parameter, an imaging mode, a beamformer setting, and an examination preset.

Example 20 is an ultrasound system comprising: an ultrasound machine configured in a configuration state as part of an ultrasound examination that includes workflow steps, the configuration state including at least one of an imaging parameter, an imaging mode, a beamformer setting, and an examination preset; and a processor system. The processor system is configured to: receive a user selection of a delimiter event; record, during the ultrasound examination, protocol data including the configuration state and the workflow steps; stop, based on an occurrence of the delimiter event, the recording of the protocol data; and generate an ultrasound protocol based on the protocol data.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in some embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

We claim:

1. An ultrasound machine comprising:
a display device configured to display a user interface that includes:
an ultrasound image generated as part of a current ultrasound examination performed using the ultrasound machine; and
an ultrasound protocol generated with the ultrasound machine based on workflow steps of the current ultrasound examination, the ultrasound image, and a configuration state of the ultrasound machine when the ultrasound image is generated;
the user interface configured to receive, during the current ultrasound examination, a user edit to the ultrasound protocol;
a pressure sensor to determine when a user grabs an ultrasound scanner for use in the current ultrasound examination to cause recording of protocol data including the configuration state and the workflow steps s-based on pressure data from the pressure sensor that is positioned on an enclosure extending between a distal end portion and a proximal end portion of the ultrasound scanner; and
a transceiver configured to transmit the ultrasound protocol with the protocol data to a protocol database for use in a subsequent ultrasound examination and receive from the protocol database an additional ultrasound protocol generated during a previous ultrasound examination, wherein the transceiver is implemented to transmit the ultrasound protocol to the protocol database for use in the subsequent ultrasound examination with an additional ultrasound machine.

2. The ultrasound machine as described in claim 1, wherein the configuration state of the ultrasound machine includes at least one of an imaging parameter, an imaging mode, a beamformer setting, and an examination preset.

3. The ultrasound system as described in claim 1, wherein the workflow steps include one or more steps to generate a measurement of a patient anatomy based on image data, and the ultrasound protocol includes instructions to generate the measurement.

4. The ultrasound system as described in claim 1, wherein the workflow steps include one or more steps to generate an annotation for a patient anatomy based on image data, and the ultrasound protocol includes instructions to generate the annotation.

5. The ultrasound system as described in claim 1, further comprising the ultrasound scanner configured to transmit ultrasound at a patient anatomy and receive reflections of the ultrasound from the patient anatomy as part of the current ultrasound examination that includes the workflow steps, wherein the ultrasound scanner includes an inertial measurement unit, the protocol data includes positional data from the inertial measurement unit, and the ultrasound protocol includes instructions for placement of the ultrasound scanner based on the positional data.

6. The ultrasound system as described in claim 1, wherein the protocol data includes image data, and the ultrasound protocol includes the ultrasound image generated based on the image data.

7. The ultrasound system as described in claim 1, wherein the display device is implemented to:
receive a user instruction to stop editing the ultrasound protocol; and
return, responsive to the user instruction, the ultrasound system to a scanning state for scanning of a patient anatomy, the scanning state being disabled while the editing of the ultrasound protocol is enabled.

8. The ultrasound system as described in claim 1, wherein the display device is implemented to display an alert indicating the recording of the protocol data.

9. An ultrasound machine comprising:
a display device configured to display a user interface that includes:
an ultrasound image generated as part of a current ultrasound examination performed using the ultrasound machine; and
an ultrasound protocol generated with the ultrasound machine based on workflow steps of the current ultrasound examination, the ultrasound image, and a configuration state of the ultrasound machine when the ultrasound image is generated;
the user interface configured to receive, during the current ultrasound examination, a user edit to the ultrasound protocol;
a pressure sensor to determine when a user grabs an ultrasound scanner for use in the current ultrasound examination to cause recording of protocol data including the configuration state and the workflow steps s-based on pressure data from the pressure sensor that is positioned on an enclosure extending between a distal end portion and a proximal end portion of the ultrasound scanner; and
a transceiver configured to transmit the ultrasound protocol with the protocol data to a protocol database for use in a subsequent ultrasound examination and receive from the protocol database an additional ultrasound protocol generated during a previous ultrasound examination,
wherein the transceiver is implemented to receive the additional ultrasound protocol generated during the previous ultrasound examination by an additional ultrasound machine.

10. The ultrasound system as described in claim 9, wherein the display device is implemented to:

receive a user instruction to stop editing the ultrasound protocol; and return, responsive to the user instruction, the ultrasound system to a scanning state for scanning of a patient anatomy, the scanning state being disabled while the editing of the ultrasound protocol is enabled.

11. The ultrasound system as described in claim 9, further comprising a processor system configured to generate, based on image data, an image in a non-ultrasound style, and the ultrasound protocol includes display of the image in the non-ultrasound style.

12. The ultrasound system as described in claim 11, wherein the non- ultrasound style includes at least one of an illustration, a cartoon, and a painting.

13. The ultrasound system as described in claim 11, wherein the processor system is configured to implement a machine-learned model that transfers the image data from an ultrasound style to the non-ultrasound style to generate the image.

14. The ultrasound system as described in claim 9, further comprising a processor system configured to:

determine an occurrence of a delimiter event during the current ultrasound examination; and stop the recording of the protocol data based on the occurrence of the delimiter event.

15. The ultrasound system as described in claim 14, wherein the delimiter event includes saving image data.

16. The ultrasound system as described in claim 14, wherein the processor system is configured to implement a machine-learned model to determine the occurrence of the delimiter event.

17. A method implemented by a computing device, the method comprising:

displaying, in a user interface of a display, an ultrasound image generated as part of a current ultrasound examination performed using an ultrasound machine;

displaying an ultrasound protocol generated with the ultrasound machine based on workflow steps of the current ultrasound examination, the ultrasound image, and a configuration state of the ultrasound machine when the ultrasound image is generated;

receiving, via the user interface during the current ultrasound examination, a user edit to the ultrasound protocol;

determining when a user grabs an ultrasound scanner for use in the current ultrasound examination to cause recording of protocol data including the configuration state and the workflow steps based on pressure data from a pressure sensor that is positioned on an enclosure extending between a distal end portion and a proximal end portion of the ultrasound scanner;

transmitting, with a transceiver, the ultrasound protocol to a protocol database for use in a subsequent ultrasound examination; and receiving, from the protocol database, an additional ultrasound protocol generated during a previous ultrasound examination by an additional ultrasound machine.

18. The method as described in claim 17, wherein the configuration state of the ultrasound machine includes at least one of an imaging parameter, an imaging mode, a beamformer setting, and an examination preset.

19. The method as described in claim 17, further comprising: receiving a user instruction to stop editing the ultrasound protocol; and returning, responsive to the user instruction, the ultrasound system to a scanning state for scanning of a patient anatomy, the scanning state being disabled while the editing of the ultrasound protocol is enabled.

20. The method as described in claim 17, wherein the workflow steps include one or more steps to generate a measurement of a patient anatomy based on image data, and the ultrasound protocol includes instructions to generate the measurement.

*   *   *   *   *